United States Patent
Kimoto (10) Patent No.: US 8,655,072 B2
(45) Date of Patent: Feb. 18, 2014

(54) MEDICAL IMAGE PROCESSING APPARATUS AND MEDICAL IMAGE PROCESSING PROGRAM

(75) Inventor: Tatsuya Kimoto, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 105 days.

(21) Appl. No.: 13/497,413

(22) PCT Filed: Oct. 6, 2011

(86) PCT No.: PCT/JP2011/005628
§ 371 (c)(1),
(2), (4) Date: Mar. 21, 2012

(87) PCT Pub. No.: WO2012/046451
PCT Pub. Date: Apr. 12, 2012

(65) Prior Publication Data
US 2012/0263359 A1  Oct. 18, 2012

(30) Foreign Application Priority Data
Oct. 6, 2010 (JP) ................................. 2010-226187

(51) Int. Cl.
*G06K 9/34* (2006.01)
*G06K 9/00* (2006.01)

(52) U.S. Cl.
USPC ............ 382/173; 382/130; 382/131; 382/180

(58) Field of Classification Search
USPC .......................... 382/131, 132, 173, 174, 180
See application file for complete search history.

(56) References Cited

U.S. PATENT DOCUMENTS

| 7,940,975 | B2 | 5/2011 | Nakashima et al. |
| 2005/0100203 | A1 | 5/2005 | Fujisawa |
| 2008/0063136 | A1 | 3/2008 | Ohyu et al. |
| 2009/0257550 | A1* | 10/2009 | Moriya ............................. 378/4 |

(Continued)

FOREIGN PATENT DOCUMENTS

| CN | 1988850 | 6/2007 |
| EP | 2199976 | 6/2010 |

(Continued)

OTHER PUBLICATIONS

International Search Report Issued Nov. 8, 2011 in PCT/JP11/05628 Filed Oct. 6, 2011.

(Continued)

*Primary Examiner* — Anand Bhatnagar
*Assistant Examiner* — Soo Park
(74) *Attorney, Agent, or Firm* — Oblon, Spivak, McClelland, Maier & Neustadt, L.L.P.

(57) ABSTRACT

A medical image processing apparatus includes a first extraction part, an adding part, a first specifying part, and a second specifying part. The first extraction part extracts an air region from volume data after receiving volume data representing a region including an organ under observation. The adding part adds pixel values of the pixels in the air region along a predetermined projection direction to generate projection image data representing the distribution of the added value of pixel values. The first specifying part specifies a first characteristic point from the projection image data. The second specifying part specifies, as a second characteristic point, a point on a line passing a first characteristic point in an air region.

6 Claims, 9 Drawing Sheets

(56) References Cited

U.S. PATENT DOCUMENTS

| | | | |
|---|---|---|---|
| 2010/0119129 A1 | 5/2010 | Moriya | |
| 2011/0243419 A1* | 10/2011 | Allmendinger et al. | 382/131 |
| 2012/0059252 A1* | 3/2012 | Li et al. | 600/425 |

FOREIGN PATENT DOCUMENTS

| | | |
|---|---|---|
| JP | 8 336503 | 12/1996 |
| JP | 2005 124895 | 5/2005 |
| JP | 2005 161032 | 6/2005 |
| JP | 2007 167152 | 7/2007 |
| JP | 2008 67851 | 3/2008 |
| JP | 2008 220416 | 9/2008 |
| JP | 2008-253293 | 10/2008 |
| JP | 2010 110544 | 5/2010 |
| JP | 2010 167067 | 8/2010 |

OTHER PUBLICATIONS

Chinese Office Action mailed Nov. 27, 2013 in Chinese Patent Application No. 201180002827.0.

Xue et al.; Mar. 2006; "Computer-aided Diagnosis System for Pulmonary Nodules Based on CT images"; Chinese Journal of Medicine Physics, vol. 23, No. 2, pp. 93-96.

Chen et al.; Nov. 2008; "Extraction of ROI and Quantitative Diagnosis of Thoracic High Resolution CT"; Chinese Journal of Medicine Physics, vol. 25, No. 6, pp. 895-898.

* cited by examiner

MEDICAL IMAGE PROCESSING APPARATUS AND MEDICAL IMAGE PROCESSING PROGRAM

CROSS-REFERENCE TO RELATED APPLICATION

This application is based upon and claims the benefit of priority from Japanese Patent Application No. 2010-226187, filed 10/06/2010; the entire contents of which are incorporated herein by reference.

FIELD OF THE INVENTION

The embodiment of the present invention relates to a medical image processing apparatus and a medical image processing program.

BACKGROUND OF THE INVENTION

Diagnoses have been provided by acquiring medical images using medical imaging apparatuses such as X-ray CT devices or MRI devices and observing the medical images. As an example, diagnosis of emphysema using medical images has been carried out. Regarding the diagnosis of emphysema using medical images, it is required to specify (extract) a lung field region from a medical image. The region growing method is one method for specifying (extracting) a lung field region from a medical image. The region growing method is a method by which one pixel in a region subjected to extraction is determined and taken as the start point (seed point), and pixels considered to be within the region are consecutively extracted. As described, in the region growing method, one pixel that is present in a region subjected to extraction (for example, a lung field region) simply has to be specified. Conventionally, with reference to medical images, an observer used to visually determine one pixel that is present within a lung field region. For example, an observer used to visually verify a coronal image or an axial image in which a chest portion was represented and determine one pixel that is within a lung field region.

DETAILED DESCRIPTION OF THE INVENTION

The medical image processing apparatus related to the present embodiment comprises a first extraction means, an adding means, a first specifying means, and a second specifying means. The first extraction means extracts an air region from volume data after receiving the volume data representing a region including an organ under observation. The adding means adds pixel values of the pixels within the air region in the volume data in a predetermined projection direction to generate projection image data representing the distribution of the added value of pixel values. The first specifying means specifies a first characteristic point from the projection image data. The second specifying means specifies, as a second characteristic point, a point on a line passing the first characteristic point in an air region.

Figure 1:
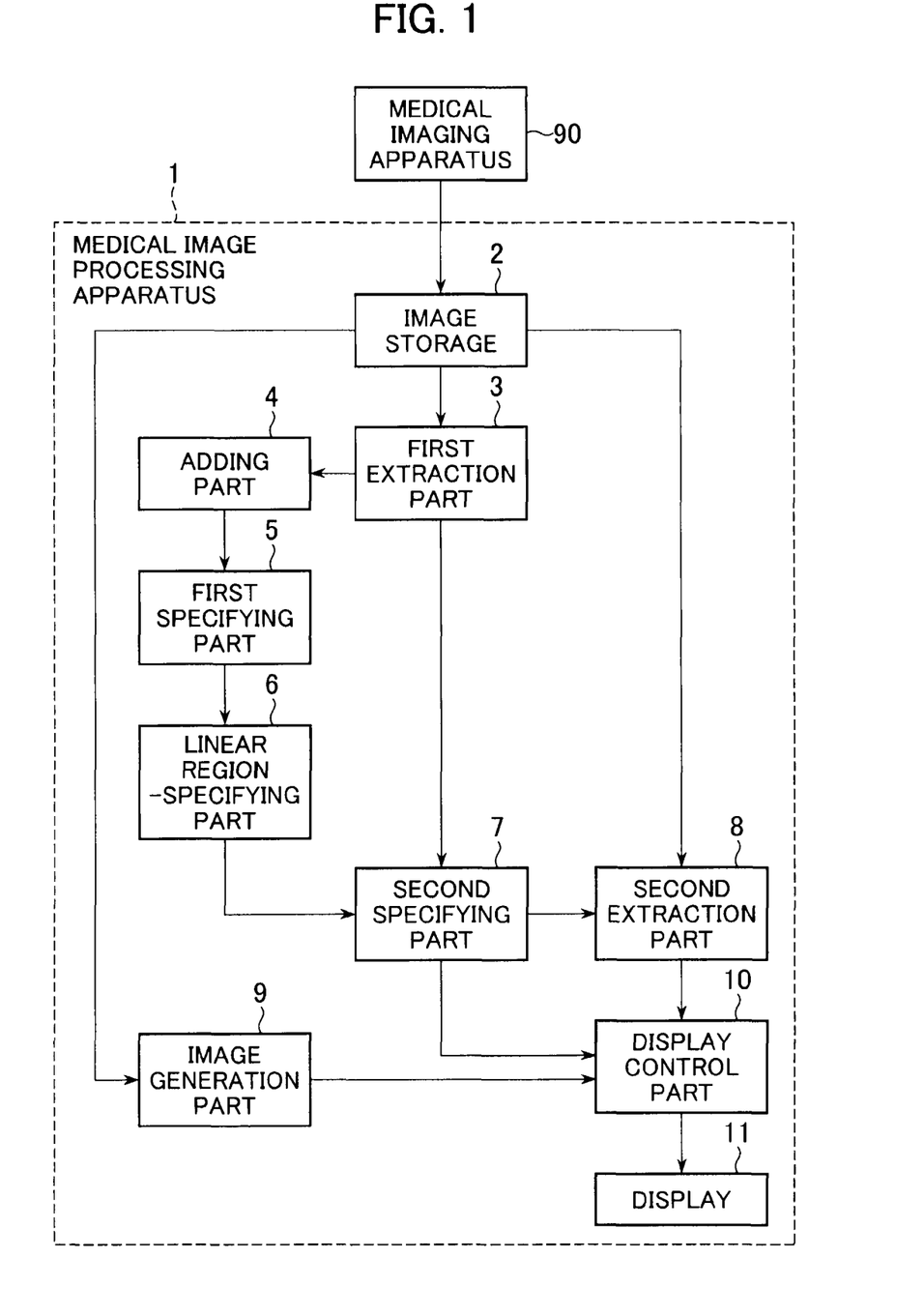
[FIG. 1] This is a block diagram of a medical image processing apparatus related to the present embodiment.

With reference to FIG. 1, a medical image processing apparatus related to the present embodiment is described. The medical image processing apparatus I related to the present embodiment is, for example, connected to a medical imaging apparatus 90.

For the medical imaging apparatus 90, imaging devices such as an X-ray CT device or an MRI device are used. The medical imaging apparatus 90 generates medical image data representing a subject by imaging the subject. For example, the medical imaging apparatus 90 generates volume data representing a three-dimensional imaging region by imaging the three-dimensional imaging region. For example, an X-ray CT device serving as the medical imaging apparatus 90 generates CT image data at a plurality of cross-sections respectively at a different location by imaging a three-dimensional imaging region. An X-ray CT device uses a plurality of CT image data to generate volume data. The medical imaging apparatus 90 outputs the volume data to the medical image processing apparatus 1. In this embodiment, with the medical imaging apparatus 90, an organ under observation such as the lungs, large intestine, or stomach is imaged in order to acquire volume data representing a region including the organ under observation. As one example, a case is described in which volume data representing a region including a lung field region is acquired by imaging a chest portion of a subject with the medical imaging apparatus 90.

The medical image processing apparatus 1 comprises an image storage 2, a first extraction part 3, an adding part 4, a first specifying part 5, a linear region-calculation part 6, a second specifying part 7, a second extraction part 8, an image generation part 9, a display control part 10, and a display 11.

The image storage 2 stores volume data generated by the medical imaging apparatus 90. It should be noted that the medical image processing apparatus 1 may also generate volume data instead of generating the volume data by the medical imaging apparatus 90. In this case, the medical image processing apparatus 1 generates volume data based on a plurality of medical image data after receiving the plurality of medical image data (for example, CT image data) generated by the medical imaging apparatus 90. In this case, the image storage 2 stores volume data generated by the medical image processing apparatus 1.

Figure 2:
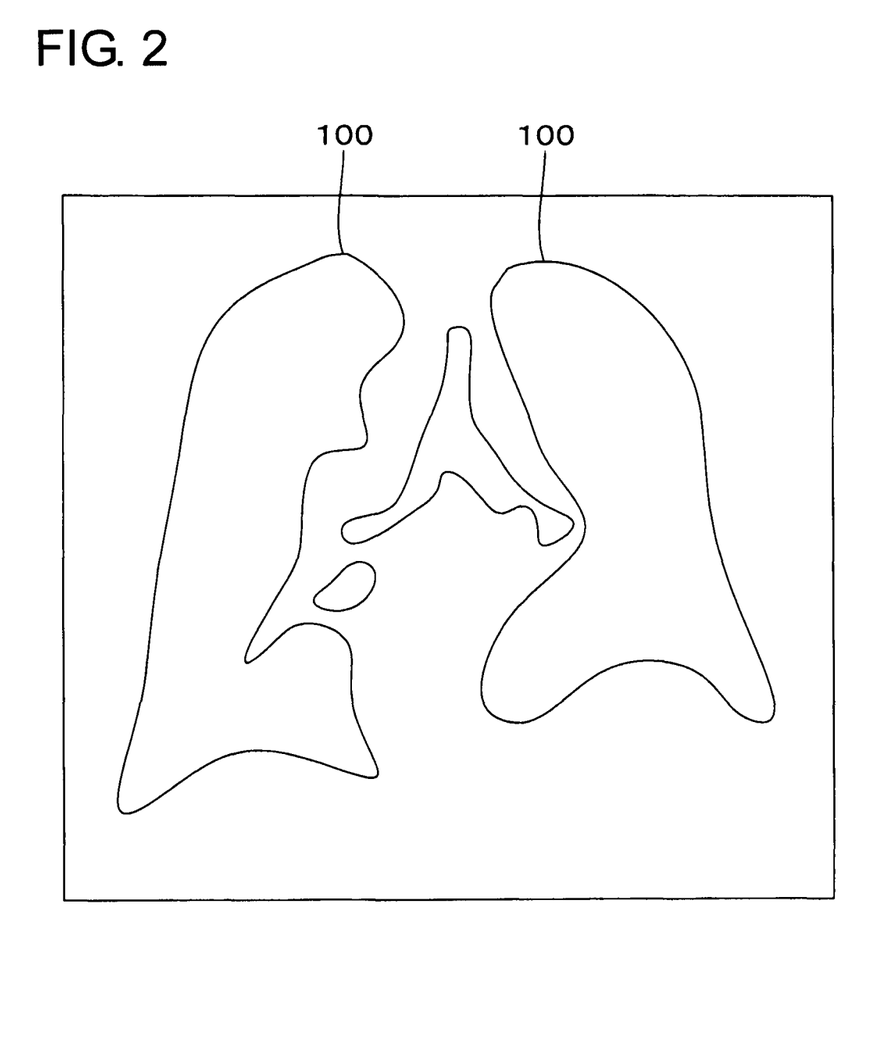
[FIG. 2] This is a drawing showing a low pixel value region.

The first extraction part 3 reads volume data from the image storage 2 and extracts a low pixel value region (air region) from the volume data by a threshold value process. For example, the first extraction part 3 extracts a low pixel value region by a binarizing process. Specifically, the first extraction part 3 extracts a region (an air region) with a low pixel value (for example, a CT value) by taking a region in which pixel values such as a CT value, a luminance value, etc. become lower than a preliminarily set threshold value as a concentration value "1" and a region in which pixel values become greater than a threshold value as a concentration value "0". The pixel value may be a CT value or may also be a luminance value. It should be noted that the range of the threshold value process is within a body surface. FIG. 2 shows an extraction result. The low pixel value region 100 shown in FIG. 2 is a three-dimensional region extracted from volume data by the first extraction part 3. The low pixel value region 100, for example, corresponds to an air region.

The adding part 4 adds a pixel value to each pixel within a low pixel value region in the volume data in a predetermined projection direction to generate projection image data representing the distribution of the added value of pixel values. Herein, a mutually and perpendicularly crossing coronal plane, axial plane, and sagittal plane are defined. The axis perpendicular to a coronal plane is the Y-axis, the axis perpendicular to an axial plane is the Z-axis, and the axis perpendicular to a sagittal plane is the X-axis. The Z-axis is equivalent to the body axis of a subject. The adding part 4 adds a pixel value to each pixel in each coronal plane in a projection direction (direction of the Y-axis) perpendicular to the coronal plane, in which the direction perpendicular to the coronal plane (direction of the Y-axis) is set to be the projection direction, and generates projection image data representing the distribution of the added value of pixel values. The projection image data is image data in which a low pixel value region of each coronal plane is added and projected onto a plane parallel to the coronal plane.

Figure 3:
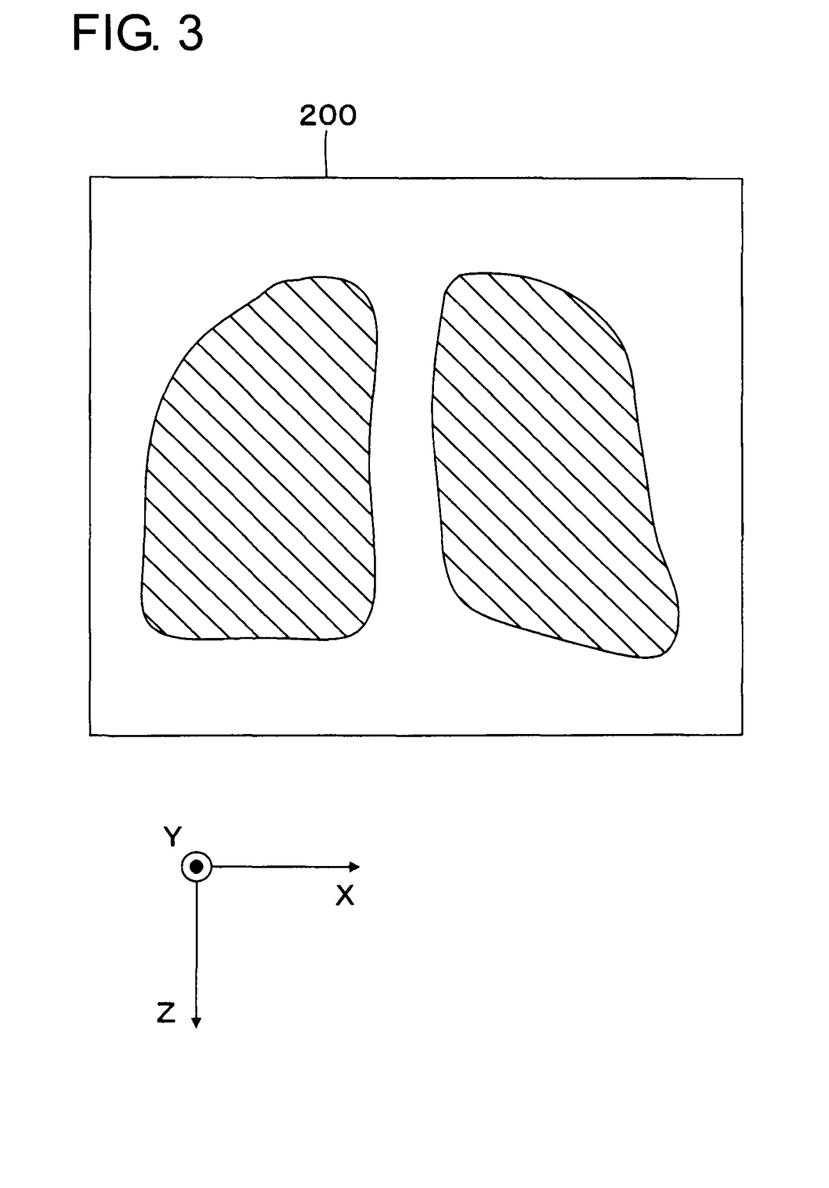
[FIG. 3] This is a drawing showing a projection image.

FIG. 3 shows one example of a projection image. The process of the adding part 4 described above may also be described as follows. An x-coordinate and a z-coordinate at a coordinate (x, y, z) are fixed and the sum of pixel values of all the pixels in the y-coordinate is regarded as the pixel value of each pixel of an xz-plane (coronal plane), making up the projection image data.

Each pixel value Map(x, z) of the projection image data may be defined by the following formula (1).

$$\mathrm{Map}(x, z) = \Sigma \mathrm{Mask}(x, y_i, z) \quad \text{Formula (1):}$$

Herein, Mask(x, y, z) is the pixel value of each pixel within a low pixel value region.

The range of the addition (range of $y_i$) is, as an example, i=1 to 512. That is, the projection image data is generated by adding projections with regard to 512 sheets of the coronal plane.

A projection image 200 shown in FIG. 3 is an image corresponding to Map(x, z) of formula (1).

Figure 4:
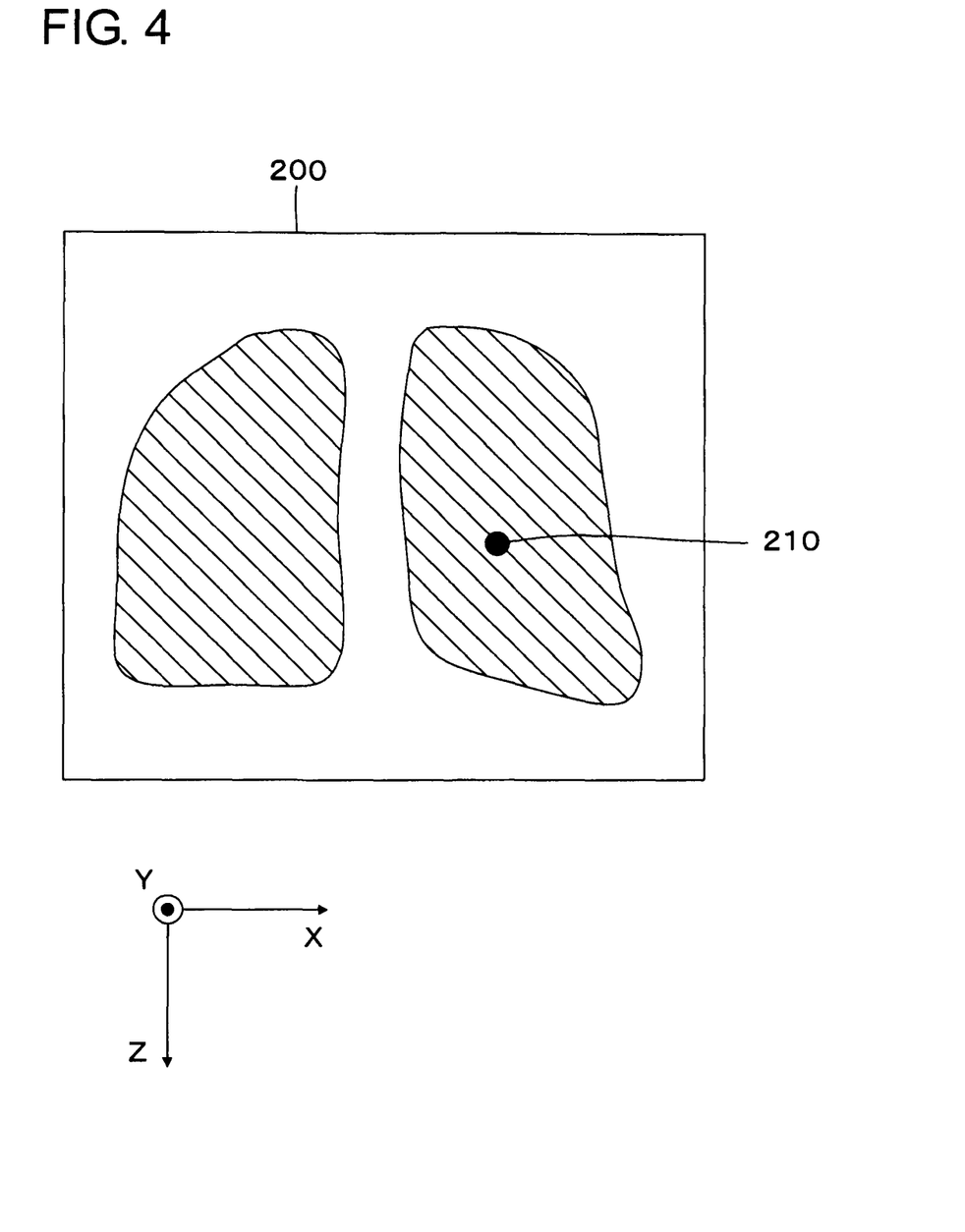
[FIG. 4] This is a drawing showing a projection image.

The first specifying part 5 specifies a first characteristic point from the projection image data. Specifically, the first specifying part 5 takes a pixel with a maximum added value (pixel value) among each pixel of the projection image data as the first characteristic point. FIG. 4 shows a projection image and a first characteristic point. In the projection image 200, the first specifying part 5 specifies a pixel ($x_m$, $z_m$) with a maximum added value as a first characteristic point 210. A pixel with the maximum added value in the projection image 200 means that the probability of the pixel being within a lung field region is high. Therefore, in this embodiment, a pixel with a maximum added value is specified in the projection image data When a lung is the subject of a process, the first specifying part 5 may also divide the projection image 200 at the center in the X-axis direction and specify a pixel with a maximum added value subjecting a projection image included in one region. That is, the first specifying part 5 may also subject each lung portion on the right side as well as the lung portion on the left side sandwiching the center in the X-axial direction so as to be treated separately. In this case, the first specifying part 5 specifies a pixel with a maximum added value in the lung portion on the right side as the first characteristic point in the lung portion on the right side and specifies a pixel with a maximum added value in the lung portion on the left side as the first characteristic point in the lung portion on the left side. The first specifying part 5 may also specify the first characteristic point subjecting only the lung portion on the right side or only the lung portion on the left side, and specify the first characteristic point in the both lung portions. For example, it is also possible for an operator to specify either the lung portion on the right side or the lung portion on the left side by an operation part (not illustrated). It should be noted that although a pixel with a maximum added value (pixel value) is taken as a first characteristic point, a pixel that has an added value within a range falling below the maximum value by a predetermined value may also be the first characteristic point.

Figure 5:
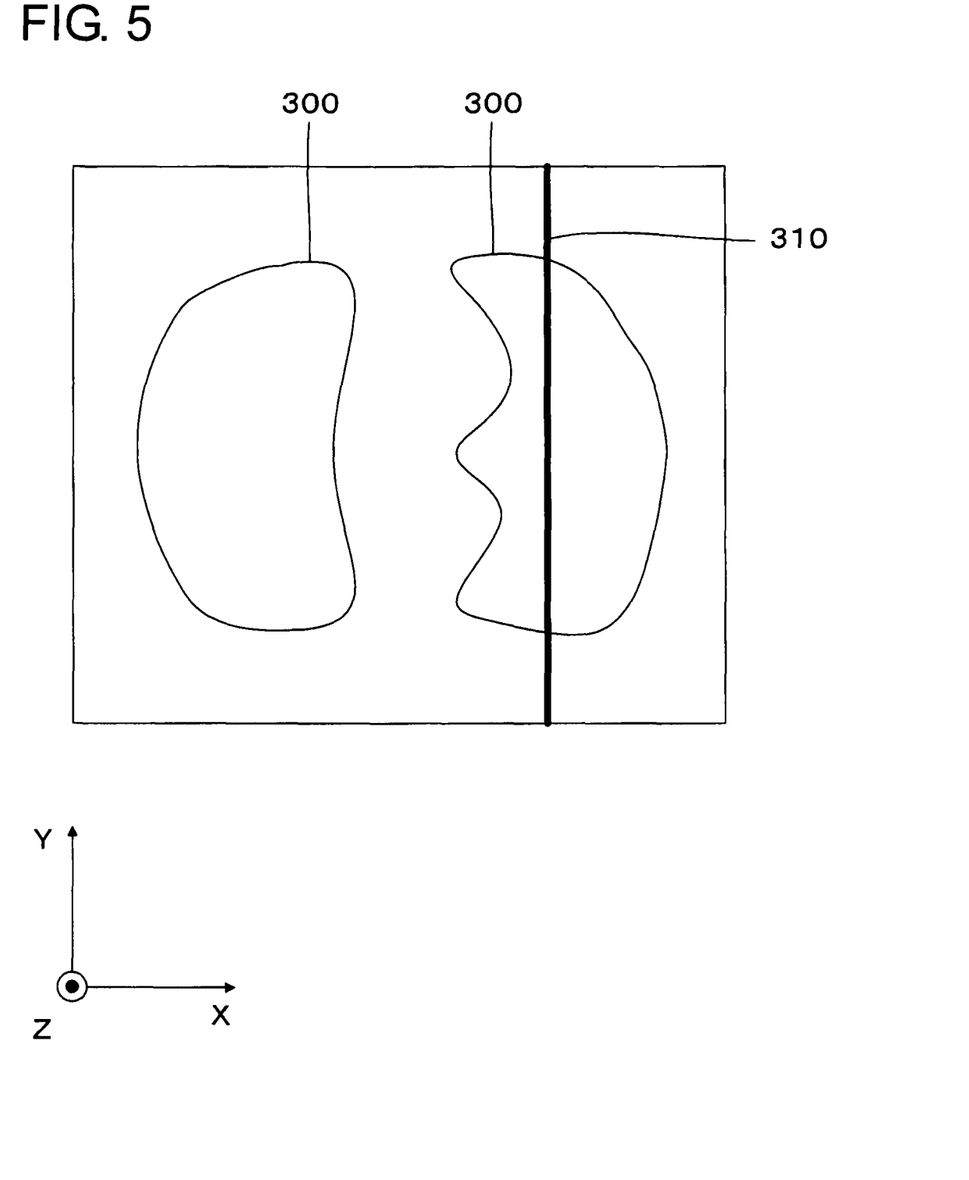
[FIG. 5] This is a drawing showing a low pixel value region and a linear region.
Figure 6:
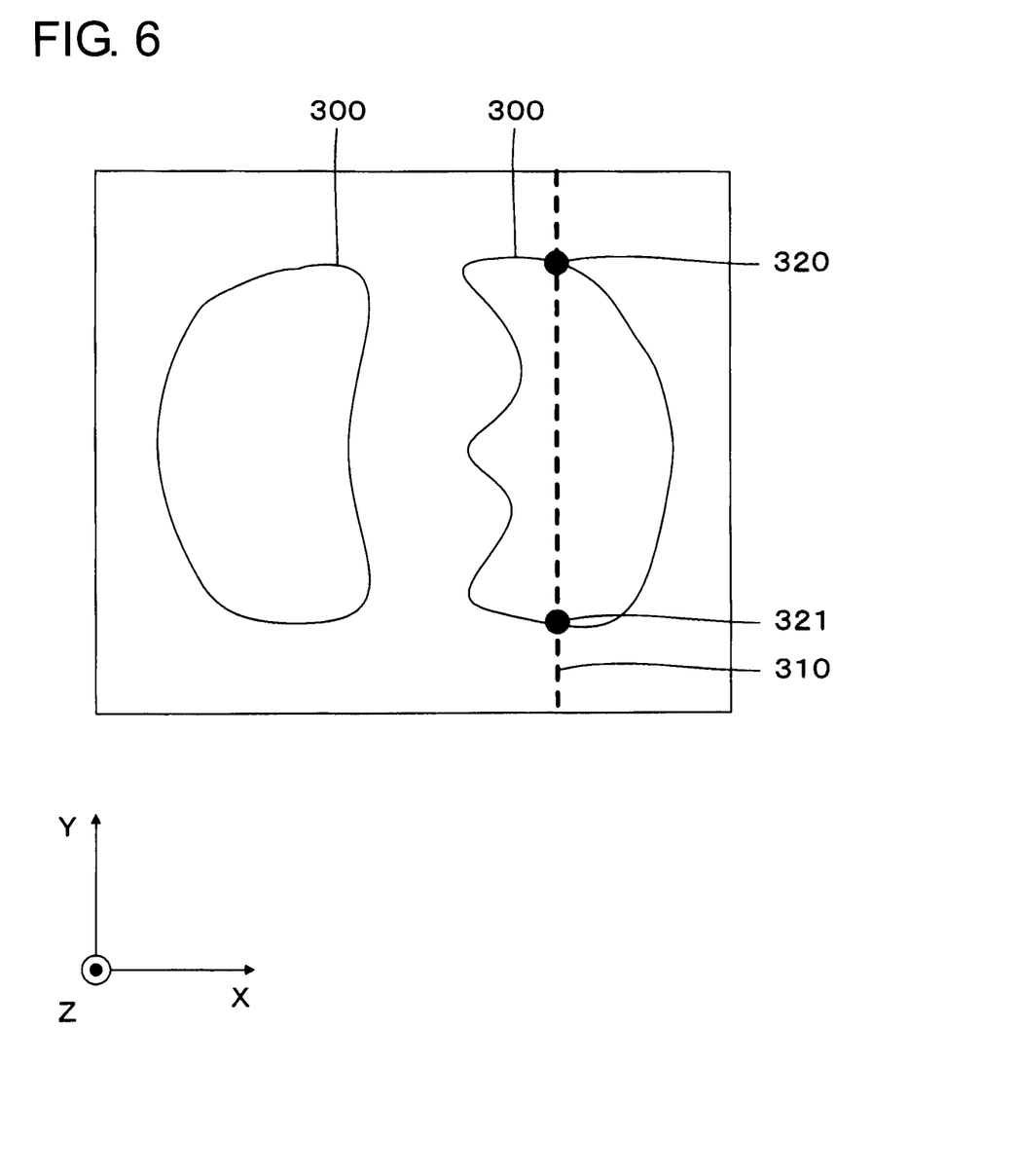
[FIG. 6] This is a drawing showing a low pixel value region and a linear region.

A linear region-calculation part 6 obtains a linear region passing the first characteristic point and extending in the abovementioned projection direction. That is, the linear region-calculation part 6 obtains a linear region by back-projecting the coordinates of the first characteristic point ($x_m$, $z_m$) in an original three-dimensional space in the projection direction. In the present embodiment, as one example, back projection is performed by the linear region-calculation part 6 in the original three-dimensional space passing the first characteristic point in the projection direction (direction of the Y-axis). The location of the linear region is represented by the coordinate group ($x_m$, $y_i$, $z_m$). FIG. 5 shows a low pixel value region and a linear region. FIG. 5 shows a low pixel value region 300 in an axial plane. A linear region 310 is represented by the coordinate group ($x_m$, $y_i$, $z_m$) passing the coordinates of the first characteristic point ($x_m$, $z_m$). As described above, because a pixel with a maximum added value in the projection image 200 is highly likely to be a pixel within a lung field region, it is highly likely that one pixel is present within a lung field region in a linear region (coordinate group ($x_m$, $y_m$, $z_m$)) to which the coordinate ($x_m$, $z_m$) of a pixel with a maximum value in the projection image 200 is projected in the three-dimensional space The second specifying part 7 obtains, as a second characteristic point, a point on a linear region in the low pixel value region. Specifically, the second specifying part 7 obtains a intersection (x, y, z) of the linear region and the contour of the low pixel value region and defines the intersection as the second characteristic point. For example, as shown in FIG. 6, the second specifying part 7 obtains a intersection 320 of the contour of the low pixel value region 300 and the linear region 310. Because the intersection 320 is highly likely to be within a lung field region in the low pixel value region 300, the pixel of the intersection 320 is defined as a pixel within the lung field region (second characteristic point). The second specifying part 7 outputs the coordinate information indicating the coordinate (x, y, z) of the second characteristic point to the display control part 10.

It should be noted that in the example shown in FIG. 6, the contour of the low pixel value region 300 and the linear region 310 cross at two intersections (intersection 320 and intersection 321). If there is a plurality of intersections, the second specifying part 7 takes one of either intersection as the second characteristic point. For example, the operator may use an operation part (not illustrated) to designate one intersection among a plurality of intersections. The display control part 10 described later may cause a display 11 to display a mark representing the second characteristic points in an overlapping manner with a medical image so that the operator simply has to designate a desired intersection using the operation part.

Furthermore, as described above, regarding points on a linear region in a low pixel value region, a pixel within a lung field region is likely to be present. Therefore, the second specifying part 7 may take an arbitrary point in a linear region as the second characteristic point in a low pixel value region.

Although a point on a line extending in the projection direction passing the first characteristic point is specified as the second characteristic point, a line for specifying the second characteristic point is not limited to the one extending in the projection direction. That is, a point on a line passing the first characteristic point simply has to be specified as the second characteristic point.

The second extraction part 8 extracts a lung field region from volume data, for example, using a region growing method. In the present embodiment, the second extraction part 8 receives the coordinates of the second characteristic point (x, y, z) from the second specifying part 7 and reads the volume data from the image storage 2. Subsequently, the second extraction part 8 extracts, from the volume data, a pixel considered to be a lung field region in which the second characteristic point is the start point (seed point) of the region growing method. The second extraction part 8 outputs, to the display control part 10, lung field region image data representing an image of the lung field region.

The image generation part 9 reads volume data from the image storage 2 and generates three-dimensional image data by subjecting the volume data to volume rendering. Otherwise, it is also possible for the image generation part 9 to generate image data (MPR image data) in an arbitrary cross-section by subjecting the volume data to MPR processing (Multi Planar Reconstruction). The image generation part 9 outputs medical image data such as three-dimensional image data or MPR image data to the display control part 10.

Figure 7:
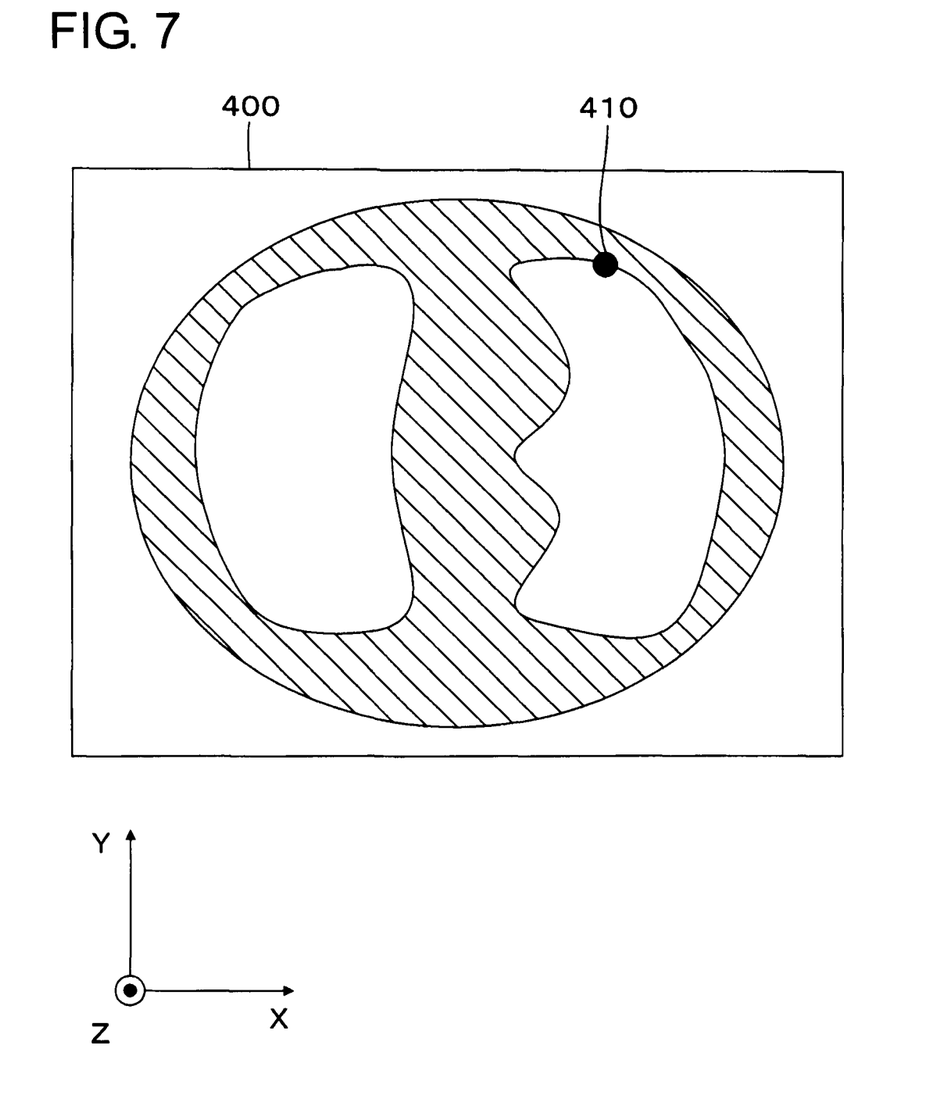
[FIG. 7] This is a drawing showing a medical image.
Figure 8:
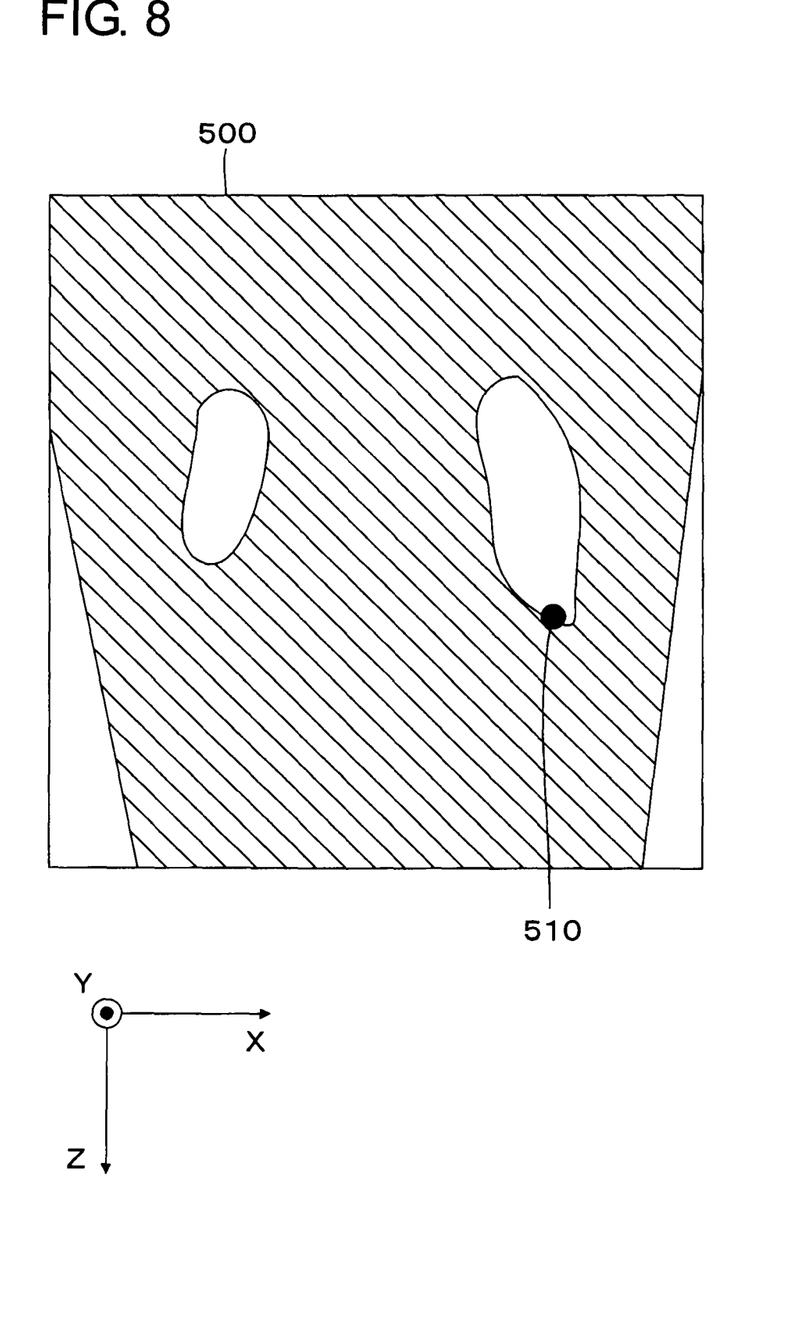
[FIG. 8] This is a drawing showing a medical image.

The display control part 10 receives the medical image data from the image generation part 9 and causes the display 11 to display medical images based on the medical image data. Furthermore, the display control part 10 may also receive the coordinate information of the second characteristic point from the second specifying part 7 and cause the display 11 to display a mark representing the second characteristic point in an overlapping manner with a medical image. FIG. 7 and FIG. 8 show one example of a medical image. For example, as shown in FIG. 7, the display control part 10 causes the display 11 to display a mark 410 representing a second characteristic point in an overlapping manner with an axial image 400. Moreover, as shown in FIG. 8, it is also possible for the display control part 10 to cause the display 11 to display a mark 510 representing the second characteristic point in an overlapping manner with a coronal image 500. It should be noted that if there are a plurality of second characteristic points, the display control part 10 may also cause the display 11 to display a mark representing each of the plurality of second characteristic points in an overlapping manner with a medical image.

Furthermore, it is also possible for the display control part 10 to receive lung field region image data representing an image of the lung field region from the second extraction part 8 and cause the display 11 to display an image representing the lung field region.

A monitor such as a CRT, a liquid crystal display, etc. constitutes the display 11. The display 11 displays medical images, a lung field region, etc.

Each function of the abovementioned first extraction part 3, adding part 4, first specifying part 5, linear region-calculation part 6, second specifying part 7, second extraction part 8, image generation part 9, and display control part 10 may also be executed by a program. As one example, a processing device (not illustrated) such as a CPU, GPU, ASIC, etc. and a storage (not illustrated) such as ROM, RAM, HDD, etc. may also respectively constitute the first extraction part 3, adding part 4, first specifying part 5, linear region-calculation part 6, second specifying part 7, second extraction part 8, image generation part 9, and display control part 10. The storage stores: a first extracting program for executing the function of the first extraction part 3, an adding program for executing the function of the adding part 4, a first specifying program for executing the function of the first specifying part 5, a linear region calculation program for executing the function of the linear region-calculation part 6, a second specifying program for executing the function of the second specifying part 7, and an image generation program for executing the function of the image generation part 9, and a display control program for executing the function of the display control part 10. A processor such as CPU executes each program stored in the storage to perform the function of each part. The first extracting program, the adding program, the first specifying program, the linear region calculation program, and second specifying program constitute one example of a "medical image processing program."

Figure 9:
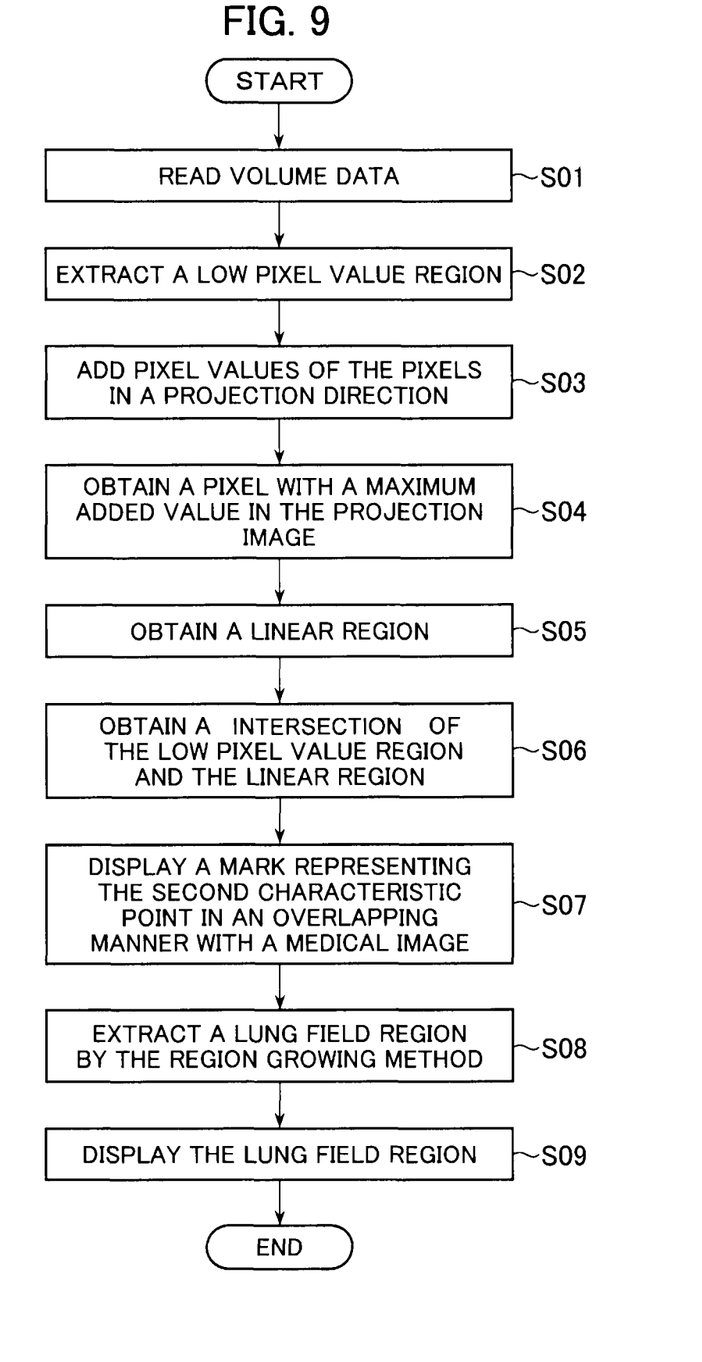
[FIG. 9] This is a flow chart showing the operations of a medical image processing apparatus related to the present embodiment.

With reference to FIG. 9, operations of the medical image processing apparatus 1 related to the present embodiment are described.

In step S01, the first extraction part 3 reads volume data from the image storage 2.

In step S02, the first extraction part 3 extracts a low pixel value region (air region) from the volume data by a threshold process.

In step S03, the adding part 4 adds a pixel value to each pixel within a low pixel value region in the volume data in a predetermined projection direction to generate projection image data representing the distribution of the added value of the pixel values. As one example, the adding part 4 adds, in the projection direction (direction of the Y-axis), a pixel value to each pixel in each coronal plane to generate projection image data representing the distribution of the added value of the pixel values, in which a direction perpendicularly crossing the coronal plane (direction of the Y-axis) is the projection direction.

In step S04, the first specifying part 5 takes a pixel with a maximum added value (pixel value) among each pixel in the projection image data as the first characteristic point ($x_m$, $z_m$).

In step S05, the linear region-calculation part 6 obtains a linear region ($x_m$, $y_i$, $z_m$) by back-projecting the coordinates ($x_m$, $z_m$) of the first characteristic point in the original three-dimensional space in the projection direction (direction of the Y-axis). That is, the linear region-calculation part 6 obtains a linear region extending in the projection direction passing the first characteristic point.

In step S06, the second specifying part 7 obtains a intersection (x, y, z) of the low pixel value region and the linear region and defines the intersection as the second characteristic point. Because the intersection is highly likely to be within a lung field region in the low pixel value region, the pixel of the intersection is defined as a pixel (second characteristic point) within the lung field region.

In step S07, the image generation part 9 reads volume data from the image storage 2 to generate medical image data based on the volume data. The display control part 10 causes the display 11 to display a mark representing the second characteristic point in an overlapping manner with a medical image. For example, the display control part 10 causes the display 11 to display a mark representing a second characteristic point in an overlapping manner with an axial image or a coronal image.

In step S08, the second extraction part 8 reads volume data from the image storage 2 and extracts, from the volume data, a pixel that is considered to be a lung field region in which the second characteristic point (x, y, z) is the start point (seed point) of the region growing method.

In step S09, the display control part 10 causes the display 11 to display an image representing the extracted lung field region.

It should be noted that the process of step S07 and the process of step S08 may be reversed in order or also be conducted simultaneously. Moreover, the processes of step S08 and step S09 may be executed without executing the process of step S07 and it is also possible to execute the process of step S07 without executing the processes of step S08 and step S09.

As described thus far, according to the medical image processing apparatus 1 related to the present embodiment, it becomes possible to automatically determine one pixel (second characteristic point) included in a lung field region. Consequently, it becomes possible to automatically extract the lung field region. As a result, the effort required to visually determine one pixel included in the lung region may be omitted while also reducing the time for diagnosis.

Furthermore, the reproducibility for specifying one pixel (second characteristic point) becomes higher in comparison to visual determination. Consequently, because the reproducibility for extracting a lung field region may also be higher, the same region may anatomically be extracted, allowing it to be utilized for diagnosis of the prognostic progress.

Moreover, because one pixel (second characteristic point) included in a lung field region may automatically be determined, it becomes possible to reduce errors among observers as well as errors within a single observer. As described, diagnosis may be supported regardless of the experience of the observers.

It should be noted that a case of extracting a lung field region is described in the present embodiment but even in case of subjecting the large intestine or stomach, a region such as the large intestine or stomach may be extracted by executing the above process.

Furthermore, the medical imaging apparatus 90 may also have a function of the medical image processing apparatus 1.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

EXPLANATION OF THE SYMBOLS 1 medical image processing apparatus
2 image storage
3 first extraction part
4 adding part
5 first specifying part
6 linear region-specifying part
7 second specifying part
8 second extraction part
9 image generation part
10 display control part
11 display

What is claimed is:

1. A medical image processing apparatus comprising:
a first extraction means that extracts an air region from volume data after receiving volume data representing a region including an organ under observation,
an adding means that adds pixel values of pixels within the air region in the volume data along a predetermined projection direction to generate projection image data representing the distribution of the added value of the pixel values,
a first specifying means that specifies a first characteristic point from the projection image data, and
a second specifying means that specifies, as a second characteristic point, a point on a line passing the first characteristic point in the air region.

2. The medical image processing apparatus according to claim 1, wherein the second specifying means obtains a intersection of the line and the contour of the air region as the second characteristic point.

3. The medical image processing apparatus according to claim 1, wherein the first specifying means obtains a pixel with a maximum added value among the pixels of the projection image data as the first characteristic point.

4. The medical image processing apparatus according to claim 1, further comprising a second extraction means that extracts the organ under observation from the volume data by a region growing method in which the second characteristic point is the start point.

5. The medical image processing apparatus according to claim 1, further comprising a display controlling means that causes a display means to display a medical image based on the volume data by overlapping with a mark that represents the second characteristic point.

6. A non-transitory computer readable medium storing a medical image processing program that, when executed by a computer, causes the computer to execute:
a first extraction function that extracts an air region from volume data that represents a region including an organ under observation;
an adding function that adds pixel values of the pixels within the air region in the volume data along a predetermined projection direction to generate projection image data representing the distribution of the added value of the pixel values;
a first specifying function that specifies a first characteristic point from the projection image data; and
a second specifying function that specifies, as a second characteristic point, a point on a line passing the first characteristic point in the air region.

* * * * *